United States Patent
Wang

(10) Patent No.: US 9,708,638 B1
(45) Date of Patent: Jul. 18, 2017

(54) PROTEASE ASSAY METHOD USING SITE-SPECIFIC FLUORESCENCE DYE LABELED PROTEIN AS SUBSTRATE

(71) Applicant: EZBiolab, Carmel (IN)

(72) Inventor: Yi Wang, Southbury, CT (US)

( * ) Notice: Subject to any disclaimer, the term of this patent is extended or adjusted under 35 U.S.C. 154(b) by 55 days.

(21) Appl. No.: 14/451,974

(22) Filed: Aug. 5, 2014

(51) Int. Cl.
  *G01N 33/53* (2006.01)
  *C12Q 1/37* (2006.01)
(52) U.S. Cl.
  CPC ........... *C12Q 1/37* (2013.01); *G01N 2500/04* (2013.01)
(58) Field of Classification Search
  None
  See application file for complete search history.

(56) References Cited

PUBLICATIONS

Cleavage of Pro-Tumor Necrosis Factor Alpha by ADAM Metallopeptidase Domain 17: A Fluorescense-Based Protease Assay Cleaves Its Natural Protein Substrate; Chengquan Zhang, Li Zheng, John Nurnberg, Binetti M. Vacari, Jianzhong Zhou, Yi Wang; Analytical Biochemistry 445 (2014) 14-19.

*Primary Examiner* — Jacob Cheu
(74) *Attorney, Agent, or Firm* — DeLio, Peterson & Curcio, LLC; Kelly M. Nowak

(57) ABSTRACT

A method for a fluorescence based assay that includes providing a full length protein substrate, attaching a detection component to a specific site of the full length protein substrate to provide a site-specifically labeled full length protein substrate, interacting the site-specifically labeled full length protein substrate with an analyte of interest; and performing an assay for drug discovery using the site-specifically labeled full length protein substrate and the analyte of interest.

20 Claims, 16 Drawing Sheets

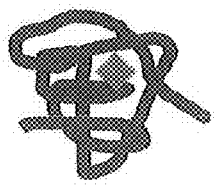
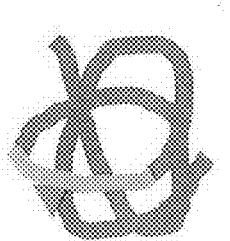
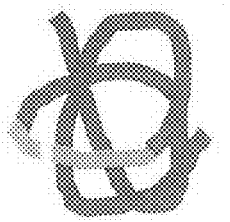
FIG. 17

PROTEASE ASSAY METHOD USING SITE-SPECIFIC FLUORESCENCE DYE LABELED PROTEIN AS SUBSTRATE

BACKGROUND OF THE INVENTION

1. Field of the Invention

The present invention relates to assays, and in particular to, protease assays using site-specifically labeled fluorescent full-length protein substrates or an independently folded domain of a protein as substrates.

2. Description of Related Art

Despite natural substrates of proteases in living cells being full-length proteins, most proteases assay methods used in biological research and drug discovery employ short peptides as substrates. Peptides are small fragments of a protein (i.e., its sequence is derived from proteins). Although a peptide shares the similar or identical amino acid sequence with the corresponding segment of its parent protein, it lacks many key structural and functional features since it does not have the tertiary folding of the protein. As a result, there are serious drawbacks in using peptide-based assays for screenings, leads optimization and structure-activity relation studies to discover drugs that target proteases.

Further, the sequence of a peptide substrate is designed to be similar to that around the cleavage site of the substrate protein to give a degree of specificity. In known assays, the protein is labeled by a fluorescence dye and a quencher conjugated at opposite ends of such peptide. However, when the peptide is cleaved by a protease into two fragments, the dye and quencher become decoupled resulting in an increase of fluorescence intensity. These types of known assays are widely adopted and used as standard assay methods for almost all proteases for compound screen and structure-activity relationship driving in drug discovery, as well as kinetic and mechanism studies in biological research. However, since a short linear peptide does not have the specific conformation of its parent protein, such assays suffer serious drawbacks.

One of the drawbacks of assays using short linear peptides as the substrate is that often interaction between a protease and a substrate protein are not limited to interactions between the active sites of the enzyme and the cleavage site of the protein. Other parts of proteins are also involved in the interaction, and the overall conformation of the substrate protein may be critical to the reaction specificity. These types of interactions do not exist for a peptide substrate.

Another drawback of using short linear peptides in assays is that the binding pockets on the surface of a substrate protein are completely lost on a peptide. As such, compounds that may bind to the substrate protein may not be able to be identified on a peptide. Additionally, the pH dependency and other reaction conditions of a peptide substrate can be very different from those of the natural protein substrate.

The above problems associated with using short linear peptides in assays may be resolved by using a natural protein substrate. However, due to the technical difficulties in handling and processing natural protein substrates they are rarely used in biochemical protease assays and methods. One of the drawbacks in using natural protein substrates for protease assays is that the reaction often needs to be stopped, and the product must be separated by electrophoresis and/or chromatograph methods. These steps are not only cumbersome and time consuming, they generate a low throughput low and the results lack quantitative accuracy.

In view of the foregoing, a need exists in the art for improved methods, systems and apparatus for performing protease assays using full-length protein substrates.

SUMMARY OF THE INVENTION

Bearing in mind the problems and deficiencies of the prior art, in one or more embodiments of the invention it is therefore an object of the present invention to provide apparatus, systems and methods for protein based assays that include providing a full length protein substrate, and attaching a detection component to a specific site of the full length protein substrate to provide a site-specifically labeled full length protein substrate. An analyte of interest that is assigned to a protease is interacted with the site-specifically labeled full length protein substrate, and then an assay is performed on the site-specifically labeled full length protein substrate and the analyte of interest for drug discovery.

In various embodiments of the invention the detection component may be a fluorescent that provides a site-specifically labeled fluorescent protein substrate. The site-specifically labeled fluorescent protein substrate may be generated by protein ligation via ligating the full length protein substrate with a fluorescence labeled peptide. In these embodiments the assays may be performed by monitoring change of fluorescence signal continuously or after the end of reaction by methods selected from fluorescence intensity and fluorescence polarization.

In the instant assays the drug discovery assay may be for discovering a compound that interacts with the analyte of interest, or alternatively, a compound that interacts with the site-specifically labeled full length protein substrate. The detection components may be a fluorescence dye, a quencher or a combination of both a fluorescence dye and a quencher.

In accordance with the invention, the full length protein substrate may be a protein that provides a site-specifically labeled protease substrate. The assay for drug discovery may be performed to discover a compound that interacts with such site-specifically labeled protease substrate.

In certain embodiments the methods for performing protein based assays may further include the steps of cleaving the full length protein substrate, followed by attaching the detection component to a specific site of the full length protein substrate. In doing so, a first end of the cleaved site may be labeled with a fluorescent, while a second end of the cleaved site, opposite to that of the first end of the cleaved site, is labeled with a quencher of the fluorescent.

In various other embodiments, the invention is directed to apparatus, systems and methods for protein based assays that include providing an independent folded domain of a protein substrate, and attaching a detection component to a specific site of the independent folded domain protein substrate. This provides a site-specifically labeled independent folded domain protein substrate. An analyte of interest that is assigned to a protease is then interacted with the site-specifically labeled independent folded domain protein substrate, and an assay for drug discovery performed using such site-specifically labeled independent folded domain protein substrate and the analyte of interest.

These apparatus, systems and methods for protein based assays may further include the steps of cleaving the independent folded domain of the protein substrate and attaching the detection component to the cleaved site thereof. A fluorescent may then be labeled to or at the first end of the cleaved site, and a quencher of the fluorescent at or to a second end of the cleaved site that is opposite to the first end of the cleaved site. The detection component may be a fluorescent that provides a site-specifically labeled fluorescent independent folded domain of the protein substrate. The assay may be for drug discovery to discover a compound that interacts with the protease.

The independent folded domain of the protein substrate may be a protease, whereby the assay is for drug discovery to discover a compound that interacts with such protease.

In the various assays of the invention, the detection component may be a fluorescence dye and/or its quencher. The assays may be performed by monitoring change of fluorescence signal continuously or after the end of reaction. The instant assays may be used for drug discovery to discover a compound that interacts with the analyte of interest, or alternatively, a compound that interacts with the site-specifically labeled independent folded domain of the protein substrate.

Still other objects and advantages of the invention will in part be obvious and will in part be apparent from the specification.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 17 illustrates a site-specifically labeled full-length protein interacting with a target enzyme in accordance with one or more embodiments of the invention.

DESCRIPTION OF THE PREFERRED EMBODIMENT(S)

Figure 1:
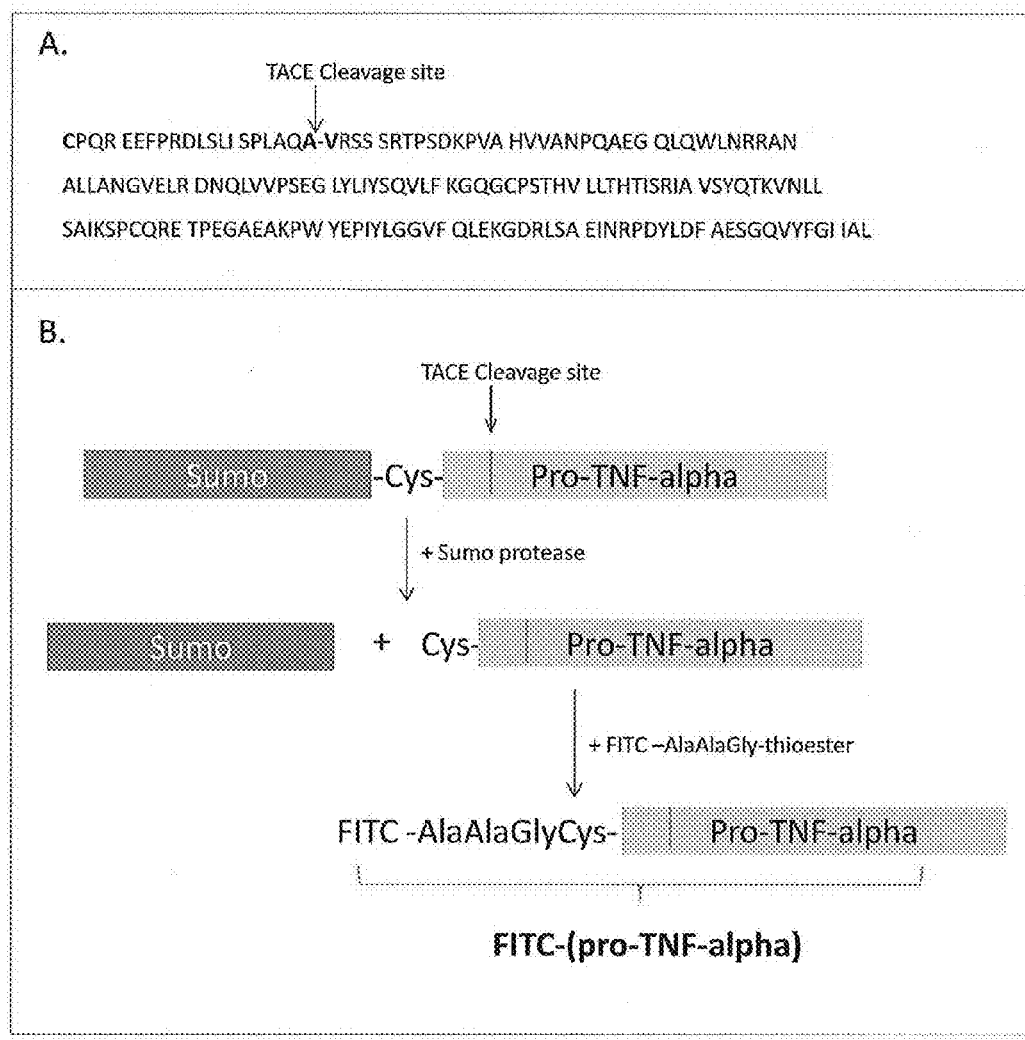
FIG. 1 illustrates a sequence and FITC labeling of pro-TNF-α, in particular, an amino acid sequence of pro-TNF-α and the N-terminal FITC labeling of pro-TNF-α of the invention.

In describing the preferred embodiment of the present invention, reference will be made herein to FIGS. 1-18 of the drawings in which like numerals refer to like features of the invention.

Generally, protein substrate based assays guide selectivity, or specificity, for one or more drugs targeting proteases. Hundreds of different proteases exist in the human body, and are grouped into several families based on their structure and/or mechanism. Proteases of the same family share similar structure and mechanism, such that, inhibitors intended to target one member of the family will often show a broad inhibition spectrum and inhibit other members of the same family. This lack of selectivity may cause undesired off-target side effects, some of which may be serious in nature. Also, since proteases often have more than one substrate in a human cell, inhibition of such proteases inevitably block other functions regulated by the enzyme. Further, inhibitors that bind to the substrate protein tend to not have these problems.

At a molecular level, selectivity is achieved through fine interaction between an enzyme molecule and its substrate protein. For many protease reactions, this interaction is determined by the overall conformation of both the enzyme and the substrate. It is also determined by the active site(s) of the enzyme and cleavage site of the substrate. A drug molecule may potentially be designed or configured to break such interactions.

In the field of protein based assays, synthetic peptides are widely used as the substrates. This is due to the ability of fluorescence dyes and quenchers to covalently conjugated to the peptide at selected sites during synthesis. A common strategy is to conjugate a fluorescence dye and its quencher at opposite sides of the cleavage site. When the peptide is cleaved by a protease, the dye is decoupled from its quencher and an increase in fluorescence intensity occurs. However, since these short peptides do not have the specific conformation of its parent protein, information gets lost in the assays using such peptides. As such, selectivity is difficult to achieve for drug molecules when studies are performed using these types of peptides. Also, since it is difficult to site-specifically label such short linear peptides it is often necessary to separate the assay products from other components of such reaction by chromatography, electrophoresis or other methods after reaction in order to analyze the reaction rate. As a result assays using short peptides are low in efficiency and output, and also tend to be costly due to the number of reagents used and processing steps.

In the various embodiments of the invention, methods, systems and apparatus are provided for performing protease assays using full-length protein substrates. In certain embodiments the invention provides methods of protein ligation to label full-length proteins in a site specific manner. In one or more embodiments the full-length proteins are labeled using fluorescent dyes in a site specific manner using protein ligation methodology. The invention also includes embodiments of using the site specifically labeled full-length proteins of the invention in protease assay methods of the invention that allows one to measure protease activity in real time by detecting the fluorescence signal. The instant protease assays are able to cleave the natural protein substrate.

Compared to using short linear peptides in assays (e.g., short synthetic peptides), full-length protein substrates offer advantages in the field of drug discovery research since cleavage of the natural protein substrate occurs. In screening to find leads of drug(s) discoveries, compounds that interact with either the target enzyme or its substrate may be detected, identified and discovered in accordance with the invention using full-length protein substrates. For instance, in certain embodiments two different classes of lead drug compounds may be identified from a single screening with the instant full-length protein substrates. These two classes of lead compounds may be detected, identified and developed separately, or alternatively, synergistically. However, in short linear peptide based assays, only those lead compounds that interact with the enzyme may be discovered since the small liner peptides do not possess the specific conformation of its parent protein, which is necessary for compound binding. The various full-length protein substrates based assays of the invention offer double the instance or chance of finding a drug candidate as compared to conventional short linear peptide based assays.

One or more embodiments of the invention are directed to methods for protein ligation to label full-length proteins in a site specific manner. In various embodiments the physiological protein substrate of a protease is specifically labeled at a desired site by a fluorescence group.

The invention is also directed to assays that use the instant labeled full-length protein as the substrate. These assays provide convenient and sensitive methods that allow measuring the activity of a protease to digest its substrate protein continuously in real time. For instance, in those embodiments that site specifically label the full-length protein with fluorescent dyes, when such specific labeled proteins are used as the substrate in a protease reaction, the reaction progress may be recorded by detecting and monitoring the change of fluorescence properties in real time and in a continuous fashion, such as, change in fluorescence intensity or fluorescence anisotropy.

Also, since it is not necessary to separate reaction products from other components in the reaction mixture when using the instant labeled full-length proteins, as compared to the need to do so for short peptides, assays using the site specifically labeled full-length proteins of the invention may be easily implemented in high throughput to screen compounds targeting protease activity. In addition to compounds binding to the protease, the instant assays simultaneously allow the discovery of compounds binding to the substrate itself, thereby increasing efficiency by allowing two-fold drug discovery and/or compound screening.

In accordance with the various embodiments, the present assays provide improved and more efficient methods for compound screening, optimization of drug discovery leads (particularly with respect to the specificity of drug discoveries). The invention also provides improved kinetic and mechanism studies of proteases for research and development, as compared to those assays using short linear peptides.

Figure 16:
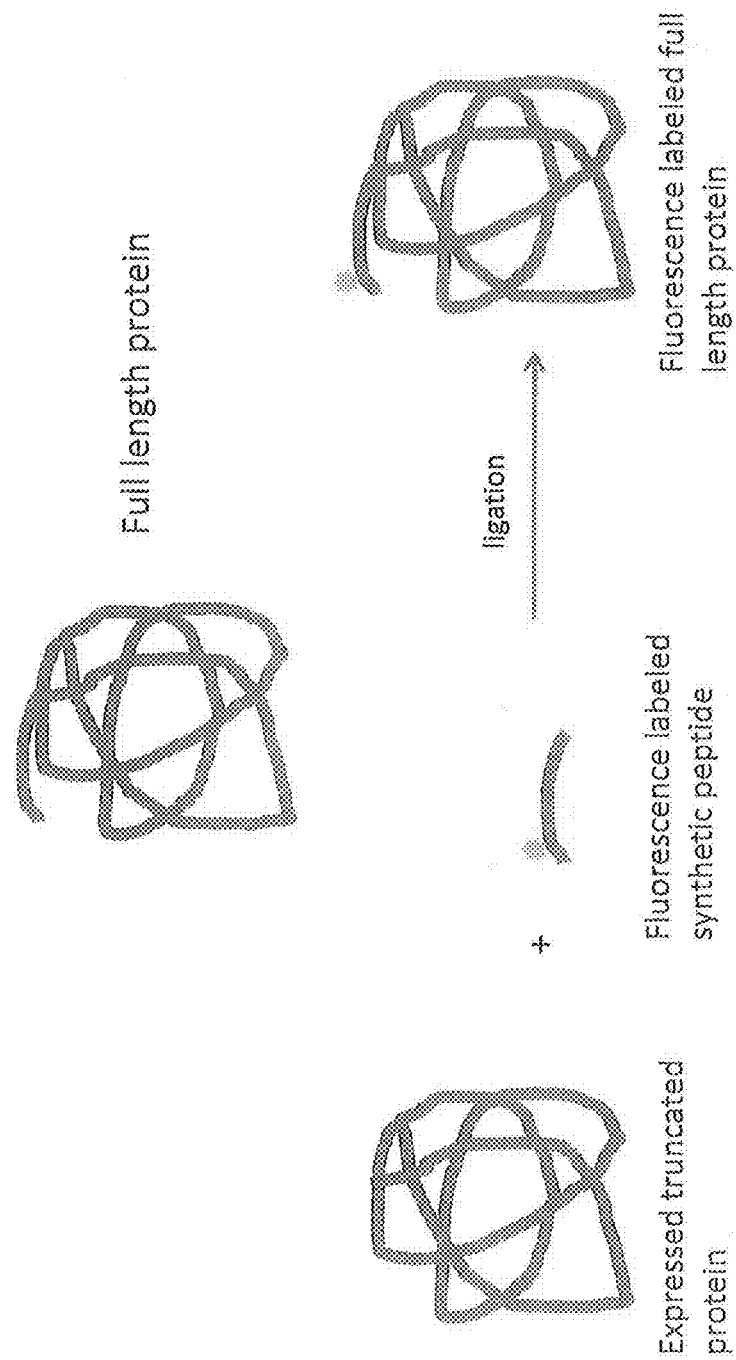
FIG. 16 illustrates protein ligation for site specific labeling of a full-length protein in accordance with one or more embodiments of the invention.
Figure 18:
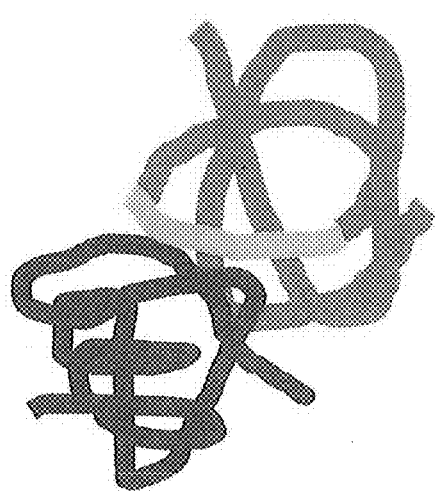
FIG. 18 illustrates a target enzyme interacted with the specifically labeled full-length protein of FIG. 17 in accordance with one or more embodiments of the invention.

In one or more embodiments, ligated and site-specifically labeled full length proteins are preferred since the fluorescence dyes and other chemical modifications (e.g., phosphorylation) may be conjugated thereto selectively. Referring to FIGS. 16-18, the instant protein ligation methods allow two protein fragments be fused into a full-length protein through a peptide bond. This allows the instant methods to site specifically label a full-length protein with a detection component including, but not limited to, a fluorescence dye, a phosphorylation modification or other modification group. Conventional approaches of peptide based assays shown in FIGS. 15A-B, merely attach a detection component or target enzyme to the short peptide.

As discussed above, as compared to the conventional peptide based assays of FIGS. 15A-B, the instant full-length protein based assays using the site-specifically labeled full length proteins as shown in FIGS. 16-18 offer several advantages for drug discovery and research. One of these advantages is the ability to identify and discover two different classes of leads from a single screening since the compounds that interact with either the target enzyme or its substrate may be discovered in full-length protein based assay of FIGS. 16-18. In short linear peptide based assays using the resultant target enzymes of FIGS. 15A-B, only those compounds/drugs that interact with the enzyme may be discovered since the linear short peptide does not have the tertiary folding of its parent peptide. The ligated full-length labeled proteins of the invention offer twice as much chance to find a drug candidate.

Further, the instant ligated full-length protein based assays of the invention provide enhanced selectivity for drugs targeting proteases, kinases, many other enzymes, and other target classes that use peptide to substitute protein as substrate or ligand. This is due to the fact that enzymes of the same class within the human body often share similar structure and mechanism, such that, a drug molecule often interferes with the function of other enzymes in addition to its target enzyme. Compounds developed from short linear peptide based assays lack this selectivity. At molecular levels, selectivity is achieved through fine interaction between enzyme molecule(s) and its substrate. This interaction is determined by the shape of the molecules, which in turn is determined by the tertiary structure of the enzyme and its substrate protein. Since short peptides do not have such a tertiary structure, these interactions do not exist in such peptide based assay and selectivity is difficult achieve therein.

Advantageously, the present ligated and site-specifically labeled full-length protein based assay for drug discovery may be used for drugs targeting proteases, kinases, many other enzymes, as well as receptor ligands, all of which are proteins in the human body. Referring to FIG. 16-17, it is shown that compounds and drugs may be discovered and assayed by interacting a site-specifically labeled full-length protein substrate with an analyte of interest, such as, a target enzyme. FIG. 18 shows a full-length protein substrate attached to the target enzyme. As can be seen by the comparison between FIG. 15B (of the peptide substrate) and FIG. 18 of the protein substrate), the short liner peptide does not have all interactions between the substrate protein and the target enzyme. However, the full-length protein substrate has many interaction sites for the target enzyme.

As such, the full-length proteins allow for attaching a detection component thereto. The detection component may be a fluorescent whereby direct observation of the fluorescence change is more reliable than filtration of SPA based radioactive isotope assay for receptor binding. Real time kinetic change may also be observed in fluorescence assay. The use of fluorescence also eliminates the radioactive waste and reduces costs.

While not meant to limit the invention, various examples of the invention are described below in accordance with one or more embodiments of the invention. It should be appreciated that numerous examples may exist in accordance with the broad concepts of the invention, the scope of which are envisioned herein in the present application. As an example, full-length protein ligation may be performed on the APP protein, the substrate of β-Secretase (BACE), which plays a central role in Alzheimer's disease. Construct for both APP and BACE have been made, and BACE has been expressed in *E. Coli*. Expression of the construct for APP has also been realized. Further examples thereof are as follows:

EXAMPLE 1

In this example, a simple and reliable fluorescence based assay is provided that detects the activity of a protease to cleave its natural protein substrate. The instant homogeneous assays implement the cleavage of pro-TNF-α by Adam 17 as an example, whereby reaction progression was recorded continuously in real time. The enzyme Adam 17 (also called TACE) is one of most extensively studied proteases. This enzyme is involved in regulation of many physiological functions. It has more than 60 reported substrates in cells and has been linked to various human diseases. Pro-TNF-α is the first identified substrate of Adam 17. TNF-α is a proven drug target to inflammatory diseases, with antibody drugs targeting TNF-α as a commercially successful protein for drug discovery. With the discovery of Adam 17, the desire increased to develop small molecule drugs targeting TNF-α related diseases that reduce TNF-α by inhibition of Adam 17. However, efforts have focused on using short peptide substrate based assays which have not been successful for generating a resultant drug discovery that treats an ailment. The target selectivity problems associated with known short peptide substrate based assays are overcome by the instant invention.

In the instant example, the overall conformation of pro-TNF-α is a determining factor for substrate specificity of Adam 17. TACE (i.e., ADAM 17) and its substrate TNF-α ("TNF-alpha") precursor Pro-TNF-α is a 212-amino acid-long transmembrane protein protein. Membrane bound TNF-α may be released to cytoplasmic through proteolytic cleavage between Ala76 and Val77 by TNF alpha converting enzyme, a metalloprotease. The cleaved soluble TNF-α is a 17 kd protein. It plays an important role in inflammation, apoptosis, and immune system development.

A synthetic TNF-α gene was cloned into a pGH plasmid and then amplified with sense primer containing Eco311 site, 5'-CAGTGGGTCTCAAGGTTGTCCGCAGCGT-GAAG-3', and the antisense primer containing Xbal site, 5'-GCGCGTCTAGATTACAGAGCGATGATACCGAAG-3', The amplified fragment was subcloned into a pE-SUMO expression vector. The construct was confirmed by DNA sequencing. The plasmid was then transformed into *Escherichia* strain BL21 (DE3) for recombinant protein expression. The expression of the target protein was initiated by addition of IPTG (Isopropyl β-D-1-Thiogalactopyranoside) to 1 mM when cell density measured by $OD_{600nm}$ reached 0.6. Cells were harvested after 3 hours of expression.

The above cell pellets were resuspended in cell lysis buffer containing 25 mM Tris-HCl, 500 mM NaCl, 2 mM Urea and 25 mM imidazole, pH8.0 and were lysed by sonication. The supernatant fraction of cell lysate containing over expressed Sumo-pro TNF-α was purified by a Ni-NTA column according to standard method. The purified fusion protein was cleaved by SUMO Ulp1 protease (the molar ratio of pro-TNF-α to SUMO Up1 was 200 to 1). The cleavage efficiency is usually more than 90% for 2 hours at 37° C. The reaction mixture was subject to another round of Ni-NTA column purification to remove cleaved Sumo, residual Sumo-pro TNF-α as well as SUMO Ulp1. FITC labeling was performed. The ligation mixture (1 mM FITC-AA-thioester, 50 mM MESNa and 5-20 mg pro-TNF-α with the final volume of 10 ml) was incubated at room temperature for 10-16 hours. The excess amount of FITC-AA-thioester was removed by a superdex S-200 column.

Cleavage of N-terminal FITC labeled pro-TNF-α was performed by a fluorescence polarization assay. The assay was performed with a SpectraMax fluorescence plate reader in 96-well format. In a typical assay, 1 µM substrate protein was preincubated at 37° C. for 20 minutes. The reaction was initiated by addition of Adam 17 to the substrate solution. The final concentration of Adam 17 was 48 nM. The total reaction volume was 100 l. The reaction buffer was 50 mM Tris-HCl, pH 7.5, 2.5 µM $ZnCl_2$, 0.005% Brij-35. In inhibition assays, the inhibitor was preincubated with its target protein for 30 minutes before reaction was initiated.

The concentration of product was calculated according to equation (1): $[P]=(F[S]-Fs[S])/(Fp-Fs)$; where $[P]$ is the concentration of product, F is the experimental recorded fluorescence polarization value, [S] is the total concentration of substrate and Fs and Fp are fluorescence polarization values of substrate and product, respectively. Fp is determined from a synthetic peptide with an identical sequence to the N-terminal fragment of the cleavage products.

In the gel assay, the reaction conditions were identical to that of fluorescence polarization assay summarized above. At each time point, 10 µl of reaction mixture was withdrawn and treated with standard SDS-PAGE loading buffer for SDS-PAGE analysis. The gel was stained by Coomassie blue and the band intensity was determined by densitometry method.

Cleavage of peptide substrates: Two peptide substrates were used in this study. PS1 is Mca-PLAQAV-Dpa-RSSSR-$NH_2$ (22), a fluorescence resonance energy transfer based substrate, the activity was measured by fluorescence intensity change upon cleavage. PS2 may be the non-fluorescence version of PS1. For PS1, in a typical assay, 10 μM substrate was preincubated at 37° C. for 20 minutes. The reaction was initiated by addition of Adam 17 to the substrate solution at the final concentration of 16 nM. The total reaction volume may be 100 μl. The reaction buffer may be 50 mM Tris-HCl, pH 9.0, 2.5 μM ZnCl$_2$, 0.005% Brij-35. In inhibition assays, inhibitor was preincubated with peptide substrate for 30 minutes. For PS2, reaction conditions were identical to PS1.

To label a fluorescence dye to the N-terminus of pro-TNF-α in a site specific manner, an N-terminal Fluorescein (FITC) labeled TNF-α was prepared. This was achieved by linking FITC-Ala-Ala-thioester to pro-TNF-α through a native chemical ligation reaction. The pro-TNF-α used in this assay may be its extracellular domain with the sequence spans from residue 58 to 233. Cleavage of this protein by Adam 17 releases a 19 mer peptide from its N-terminal end. The peptide is much smaller than the substrate protein. Therefore, a reduced fluorescence polarization value was expected upon the cleavage.

This was achieved by linking FITC-Ala-Ala-thioester to pro-TNF-α through a native chemical ligation reaction. The pro-TNF-α used in this assay may be its extracellular domain with the sequence spans from residue 58 to 233. Cleavage of this protein by Adam 17 releases a 19 mer peptide from its N-terminal end. The peptide is much smaller than the substrate protein. Therefore, a reduced fluorescence polarization value was expected upon the cleavage.

Protein ligation reaction requires a cystine residue at the N-terminal end of pro-TNF-α protein. The fusion protein is expressed in *E. Coli* and purified by a nickel column according to the standard protocol. Referring to FIG. 1, this was accomplished by fusion of pro-TNF-α to Sumo protein to create a Sumo-Cys-pro-TNF-α fusion protein. Cleavage of the fusion protein generates Cys-(pro-TNF-α). FIG. 1 shows the sequence and FITC labeling of pro-TNF-α, in particular, (A) an amino acid sequence of pro-TNF-α and (B) the N-terminal FITC labeling of pro-TNF-α of the invention.

The cleavage reaction may be performed by mixing Sumo-[pro-TNF-α] with Sumo protease in 20 mM Tris-HCL, pH 8.2 buffer for 2 hours. Final concentration of Sumo-[pro-TNF-α] and Sumo protease is about 2 mg/ml and 0.01 mg/ml respectively. After the reaction, the mixture may be passed through a nickel column again to separate Sumo protein from pro-TNF. To conjugate a fluorescence dye to the N-terminal end of the purified pro-TNF, pro-TNF-α (0.5 mg/ml) may be incubated with 10 mM FITC-AlaAlaGly-thioester in the presence of 50 mM MESNa for overnight. The reaction buffer may be 25 mM Tris-HCL, pH 8.5 containing 150 mM NaCL. After the reaction, the excess of FITC-AlaAla-thioester may be removed by a size exclusive column. The final product may be FITC-[pro-TNF-α]. There is a four-amino acid spacer AAGG between FITC and the pro-TNF-α protein.

Figure 2:
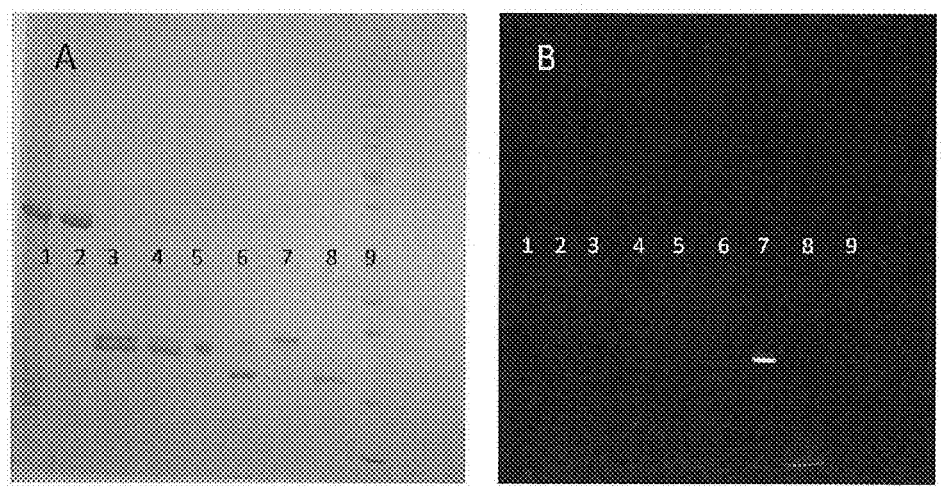
FIGS. 2A and 2B illustrate SDS PAGE of Expression, Purification, N-terminal FITC Labeling and Cleavage by TACE (also referred to as "ADAM 17") of pro-TNF-α.

FIG. 2 shows the results of FITC labeling of pro-TNF-α and its cleavage by Adam 17. The ligation product showed a strong fluorescence band at the expected position and this fluorescence band disappeared in the presence of Adam 17. This is a strong indication that FITC-AA was successfully ligated to the N-terminal end of pro-TNF-α. Coomassie blue stained gel showed a lower band corresponding to TNF-α position upon the cleavage, which confirmed the result. To estimate labeling efficiency, the protein concentration was first determined based on its band intensity in a SDS-PAGE gel. The same sample may be then determined by its OD$_{493nm}$ which is the result of FITC absorbance. The labeling efficiency may be estimated to be more than 90%. The molecular weight of Sumo protein appeared at higher than its 12.3 kd position in SDS-PAGE gel.

The results of FIGS. 2A and 2B show the SDS PAGE of expression, purification, N-terminal FITC Labeling and cleavage by ADAM 17 of Pro-TNF-α. FIG. 2A shows results of a coomassie brilliant blue staining, while FIG. 2B shows fluorescence of FITC labeled pro-TNF-α. The lanes show: Lane 1, Expression of Sumo-(pro-TNF-α) fusion protein; Lane 2, Nickel column purified Sumo-(pro-TNF-α); Lane 3, Sumo-(pro-TNF-α) cleaved by Sumo protease to yield Sumo (lower band) and pro-TNF-α (upper band); Lane 4, Sumo of lane 4 may be eluted from the 2nd nickel column; Lane 5, Pro-TNF-α of lane 4 passed through the $2^{nd}$ nickel column; Lane 6, Overnight cleavage of lane 4 pro-TNF-α by ADAM 17; Lane 7, Sample of lane 5 may be further purified by a size exclusive column; Lane 8, Cleavage of pro-TNF-α (lane 7) by BACE; and Lane 9, Molecular weight markers of the invention.

Figure 3:
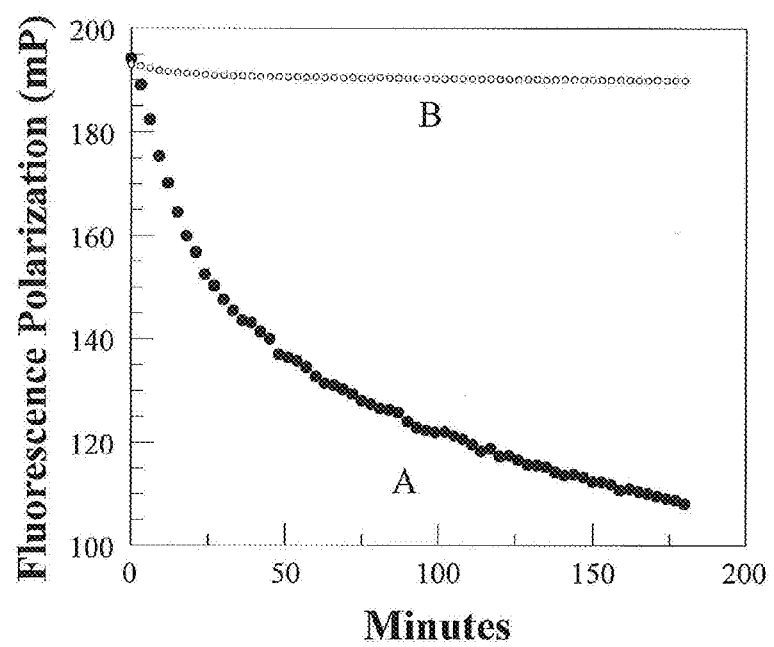
FIG. 3 illustrates a time plot of Fluorescence Polarization of FITC-(pro-TNF-α) Cleaved by ADAM 17 with (A) being – inhibitor and (B) being + inhibitor of the invention.
Figure 4:
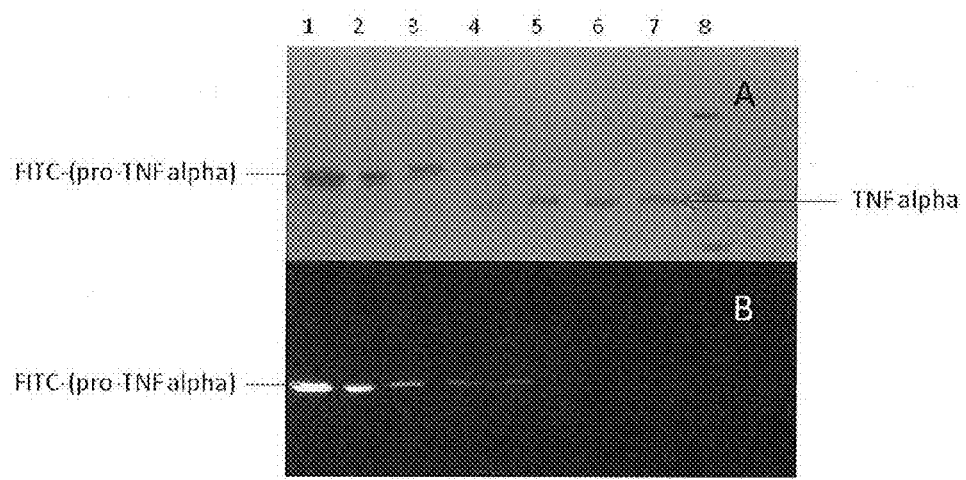
FIG. 4 illustrates SDS-PAGE Results of FITC-(pro-TNF-α) Cleaved by ADAM 17 with (A) showing Coomassie brilliant blue staining and (B) showing Fluorescence of FITC labeled pro-TNF-α.

Referring to FIGS. 3-4, cleavage of FITC-[pro-TNF-α] by ADAM 17 produces two products: FITC-C PQREEFPRDLSLISPLAQA (FITC-pro) and TNF-α protein. To initiate the cleavage reaction, 1 ul ADAM 17 (0.1 mg/ml) stock solution may be added to 100 ul FITC-[pro-TNF-α] in 20 mM Tris-HCL, PH 8.5. The final concentration of FITC-[pro-TNF-α] is about 1 uM. FIG. 3 shows a time plot of Fluorescence Polarization of FITC-(pro-TNF-α) cleaved by ADAM 17 with (A) being − inhibitor and (B) being + inhibitor of the invention. As shown, since the molecular weight of FITC-pro is significantly less than that of FITC-[pro-TNF-α], fluorescence polarization of FITC reduces when FITC-[pro-TNF-α] is cleaved by ADAM 17 as shown by Trace A in FIG. 3. Trace B in FIG. 3 shows that when N-[(2R)-2-(Hydroxamidocarbonylmethyl)-4-methylpentanoyl]-L-tryptophan methylamide, a ADAM 17 specific inhibitor, is included in the cleavage reaction at the final concentration of 10 uM, the fluorescence polarization showed little change. This confirms the specificity of the Adam 17 activity and cleavage of FITC-[pro-TNF-α] by ADAM 17.

The electrophoresis results shown in FIG. 4 validate the results of the polarization assay of FIG. 3. In FIG. 4, a fraction of the reaction mixture of FITC-(pro-TNF-α) cleaved by ADAM 17 was loaded to an SDS-PAGE gel at different time points, whereby the fluorescence signal may be measured by a fluorescence plate reader. The upper panel (A) shows the gel stained by Coomassie brilliant blue staining, and the lower panel (B) shows that of fluorescence image of FITC labeled pro-TNF-α. The lanes depicted in FIG. 4 include: Lane 1, Ligation product: FITC-(pro-TNF-α); Lane 2, Sample 1 purified by a size exclusive column; Lane 3, Cleavage reaction of FITC-(pro-TNF-α) by ADAM 17, 0 minute; Lane 4, Cleavage reaction, 40 minutes; Lane 5, Cleavage reaction, 120 minutes; Lane 6, Cleavage reaction, 180 minutes; Lane 7, Cleavage reaction, 180 minutes; Lane 8, Cleavage reaction, overnight molecular weight markers of the invention.

FIG. 4 shows that the decrease of pro-TNF-α band intensity was proportional to the increase of TNF-α band intensity, indicating that FITC-pro-TNF-α was converted into TNF-α by Adam 17. Coomassie blue staining results was consistent with fluorescence image result, in which fluorescence intensity of FITC-pro-TNF-α decreased with progression of the reaction. This further suggested the N-terminal fragment was cleaved off from the substrate protein. Protein sequencing results showed the N-terminal sequence of the cleavage product was VRSS, which confirmed that the cleavage occurred at the right site.

In this example it was found that the fluorescence intensity was unchanged before and after cleavage reaction. This allowed the concentration of product at each time point to be calculated according to equation (1) above. Another issue is that the polarization difference between subtract and product is about 110 mp. For kinetic studies, less than 10% subtract consumption may be required in order to get an initial reaction rate. This gives about 10 mP signal change. At low concentrations of subtract, it may not have sufficient signal to noise ratio for such a relatively small signal change. In such an event, integration to the full range of reaction progress curve may be necessary to extract kinetic parameters.

Figure 13:
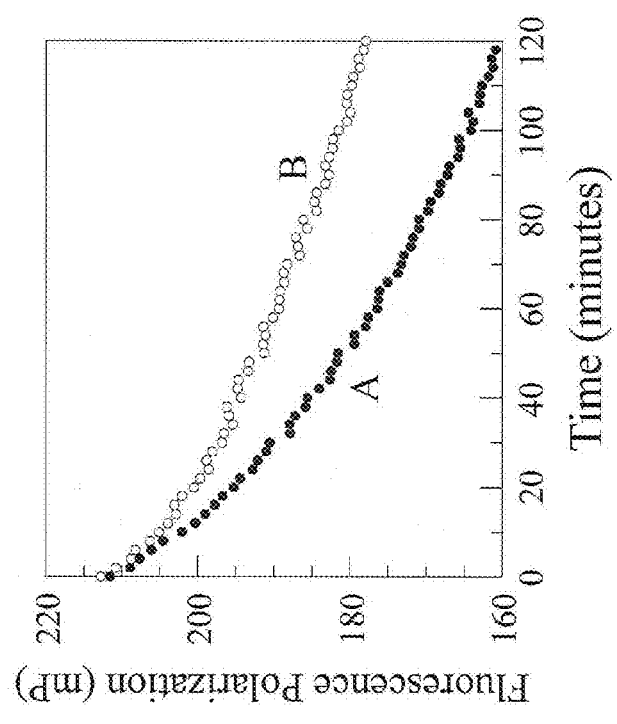
FIG. 13 illustrates the time course of Fluorescence Polarization of FITC-(pro-TNF-α) Cleaved by ADAM 17, whereby (A) shows the – inhibitor and (B) shows the + TNF-α inhibitor of the invention.
Figure 14:
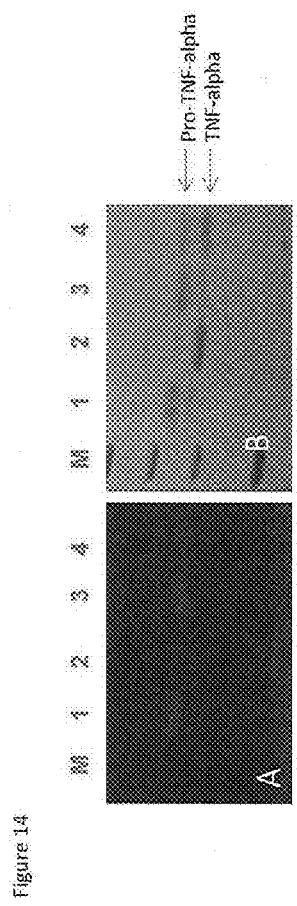
FIG. 14 illustrates the SDS-PAGE Results of FITC-(pro-TNF-α) Cleaved by ADAM 17, whereby (A) shows the Fluorescence of FITC labeled pro-TNF-α and (B) shows the Coomassie brilliant blue staining.
Figure 15:
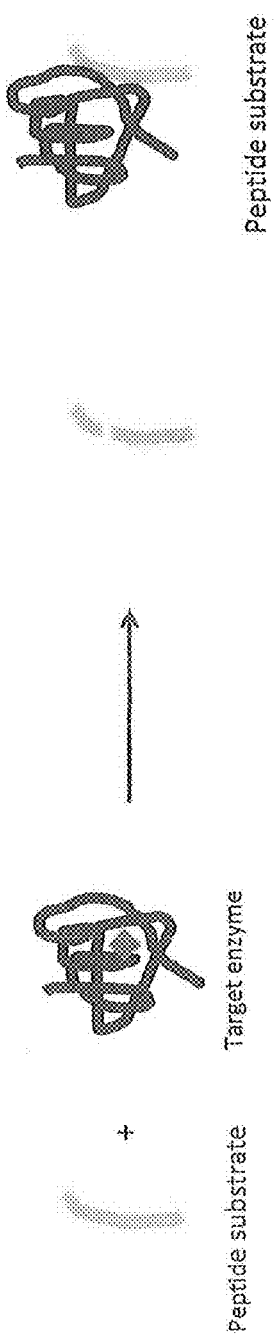
FIG. 15A-B respectively illustrate a prior art peptide substrate interacting with a target enzyme, and the resultant target enzyme.

Referring to FIGS. 13 and 14, TNF-α Inhibitor is a small molecule that blocks interaction of TNF-α with its receptor by binding to TNF-α. This compound may affect the activity of Adam 17 to convert pro-TNF-α to TNF-α. Referring to FIG. 13, it is shown that at a concentration of about 200 µM, TNF-α inhibitor reduces the reaction rate by about 40%, which is validated by the electrophoresis assay results shown in FIG. 14. To confirm that the inhibition effect of TNFα Inhibitor resulted from its binding to pro-TNF-α, the effect of the compound on Adam 17's activity was analyzed and HPLC results showed that cleavage activity of Adam 17 to the peptide substrate was not affected by the TNFα Inhibitor. This suggests that cleavage activity of Adam 17 to the peptide substrate was not affected by the TNFα Inhibitor, suggesting that the TNFα inhibitor did not interact with Adam 17. Based on the established direct binding between the compound and TNFα, it is believed that the inhibition effect is caused by the interaction of the compound to pro-TNFα.

Unlike known short peptide substrate based assays, the various full-length protease fluorescence based assay of the invention simplify such known assays, which require the reaction to be stopped and the products to be separated by chromatography, electrophoresis/blotting or other methods. The instant assays also eliminate the major hurdle for the Adam 17 assay based on its natural substrate. Compared to the currently widely used short peptide substrate based assays, the instant fluorescence labeled full length protein substrate assays are simple, quick, convenient and quantitative. Short peptide substrates and the instant full-length protease fluorescence substrates have different pH profiles which affect how such substrates conform to the reaction mechanism. Further, the various assays of the invention are easily implemented in high throughput format because of its fluorescent nature. The use of full length protein substrates in accordance with the invention overcome the limitations of short linear peptide substrates in the studies of mechanism, kinetic and inhibition of Adam 17, as well as in connection with proteases generally.

In one or more embodiments, the assays of the invention may be implemented to screen a number of compounds for identifications of protease inhibitors. In addition to identifying those inhibitors that bind to the enzyme itself, inhibitors binding to the substrate protein will also be concurrently identified by the instant assays. Such is the case as demonstrated above in Example 1 implementing the TNF-α bound small molecule. Various other examples of the invention are described below in relation to the drawings.

EXAMPLE 2

Figure 5:
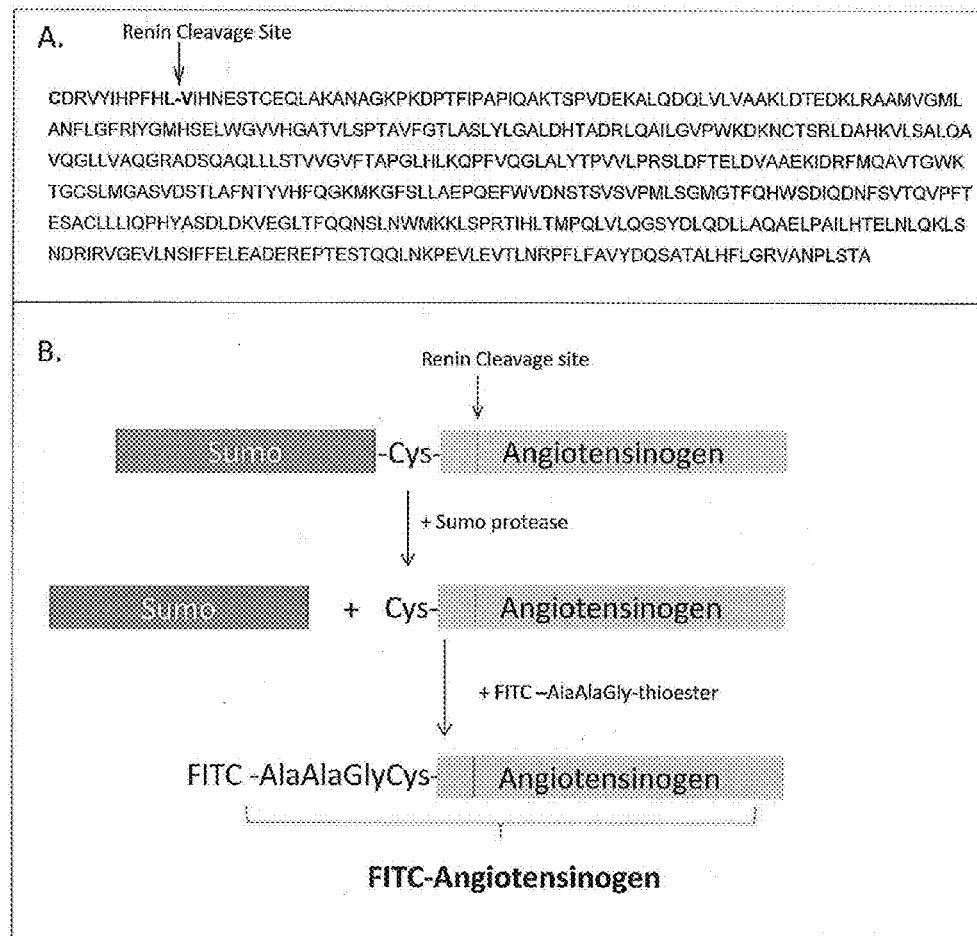
FIG. 5 illustrates the sequence and FITC labeling of Angiotensinogen, whereby (A) shows an amino acid sequence of angiotensinogen, and (B) shows the N-terminal FITC labeling of angiotensinogen of the invention.

Renin is the protease that cleaves angiotensinogen to release angiotensin I peptide. Renin-angiotensinogen system has an important role in the regulation of blood pressure. To produce an N-terminal Fluorescence dye labeled angiotensingen, a Cys residue may be added to the N-terminus of angiotensinogen. This angiotensingen may be fused to the C-terminus of Sumo protein to form Sumo-angiotensinogen fusion protein. A 6×His tag may be engineered at the N-terminal end of the fusion protein. The fusion protein is expressed in E. Coli and purified by a nickel column according to the standard protocol. This purified fusion protein may then be subjected to cleavage by Sumo protease to produce angiotensinogen with a N-terminal Cys. The cleavage reaction may be performed by mixing Sumo-angiotensinogen with Sumo protease in 20 mM Tris-HCL, pH 8.2 buffer for 2 hours. Final concentration of Sumo-angiotensinogen and Sumo protease is about 2 mg/ml and 0.01 mg/ml respectively. After the reaction, the mixture may be passed through a nickel column again to separate Sumo protein from angiotensinogen. To conjugate a fluorescence dye to the N-terminal end of the purified angiotensinogen, angiotensinogen (0.5 mg/ml) may be incubated with 10 mM FITC-AlaAlaGly-thioester in the presence of 50 mM MESNa for overnight. The reaction buffer is 25 mM Tris-HCL, pH 8.5 containing 150 mM NaCL. After the reaction, the excess of FITC-AlaAlaGly-thioester may be removed by a size exclusive column. The final product is FITC-angiotensinogen. FIG. 5 shows that there is a four-amino acid spacer CAAG between FITC and the pro-angiotensinogen.

Figure 6:
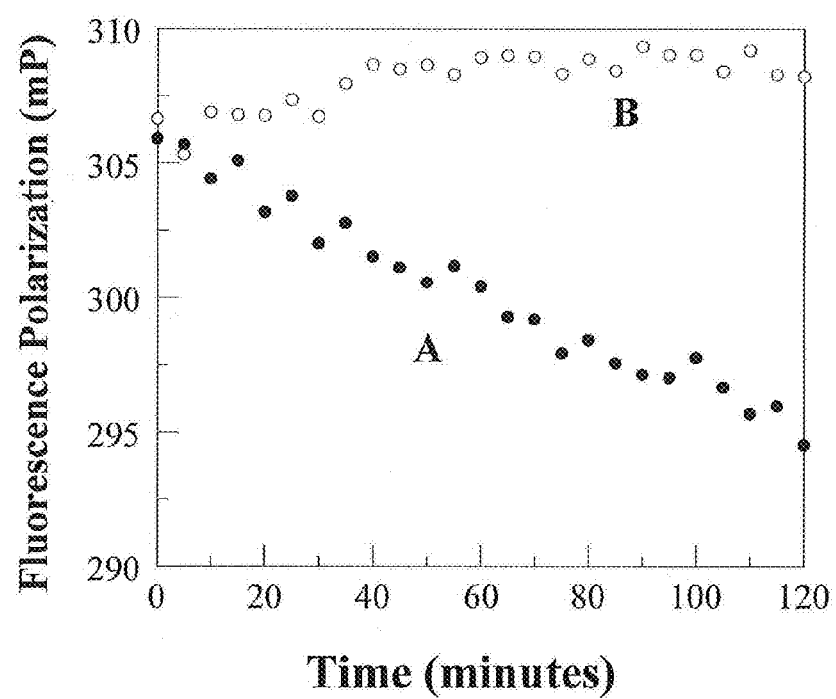
FIG. 6 illustrates the time course of Fluorescence Polarization of (5-TAMRA)-Angiotensinogen Cleaved by Renin, whereby (A) shows the – inhibitor and (B) shows the + inhibitor of the invention.

Cleavage of FITC-angiotensinogen by Renin produces two products: FITC-AAGCDRVYIHPFHL (FITC-angiotensin) and angiotensinogen protein. To initiate the cleavage reaction, 1 ul Renin (0.1 mg/ml) stock solution may be added to 100 ul FITC-angiotensinogen in 20 mM Tris-HCL, PH 8.5. The final concentration of FITC-angiotensingen may be about 1 uM. As shown by Trace A in FIG. 6, since the molecular weight of FITC-angiotensin is significantly less than that of FITC-angiotensin, fluorescence polarization of FITC reduces when FITC-angiotensin is cleaved by Renin. Trace B in FIG. 6 shows that when RRPFH-Sta-IHK, a ADAM 17 specific inhibitor, is included in the cleavage reaction at the final concentration of 10 uM, the fluorescence polarization showed little change. This confirms the specific cleavage of FITC-angiotensinogen by Renin.

Figure 7:
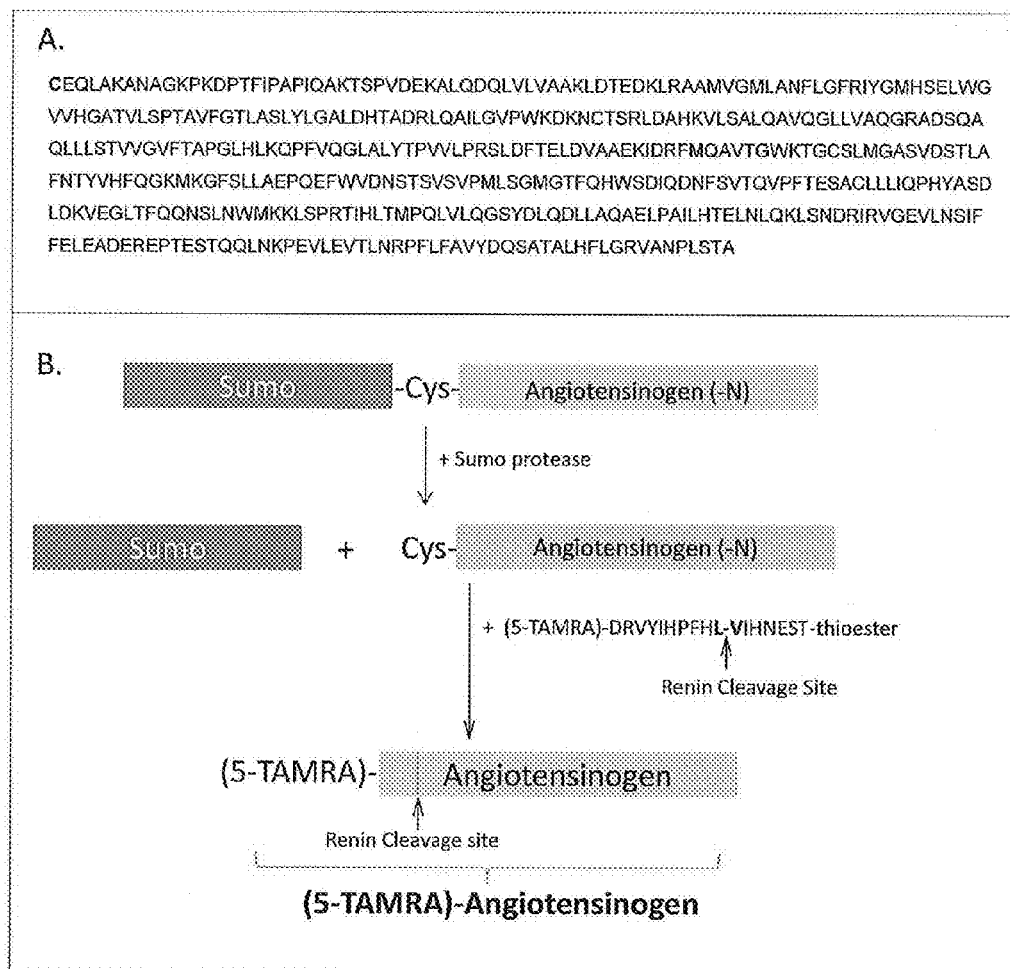
FIG. 7 illustrates the sequence and FITC labeling of the N-terminal deleted Angiotensinogen, whereby (A) shows an amino acid sequence of N-terminal deleted angiotensinogen, and (B) shows the N-terminal FITC labeling of N-terminal deleted angiotensinogen of the invention.
Figure 8:
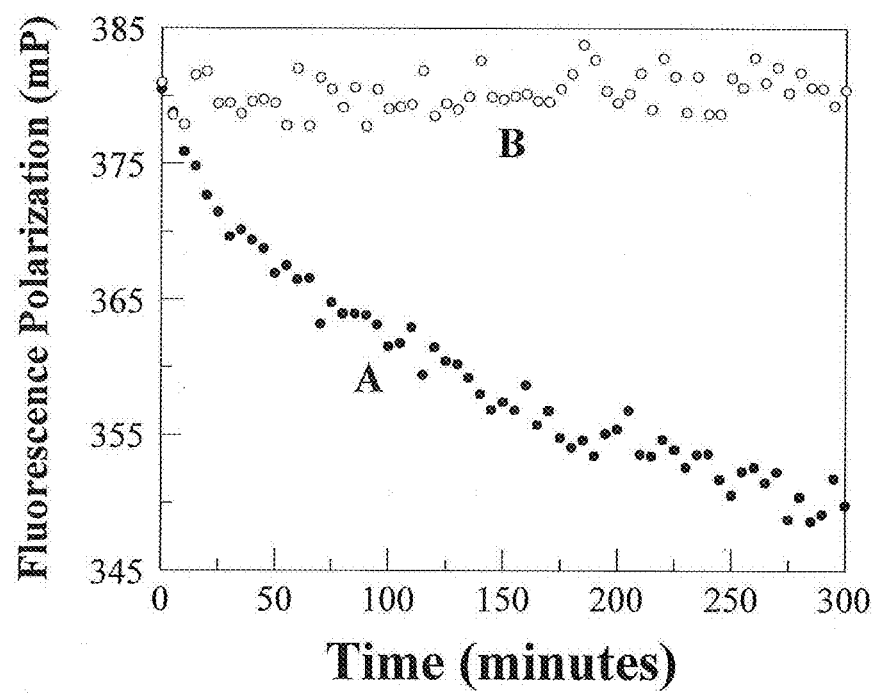
FIG. 8 illustrates the time course of Fluorescence Polarization of $2^{nd}$ (5-TAMRA)-Angiotensinogen Cleaved by Renin, whereby (A) shows the – inhibitor and (B) shows the + inhibitor of the invention.

An alternative strategy to label the full length angtensinogen is to delete 16 residues from the N-terminus of angtensinogen. This shorted angtensinogen has a Cys at its N-terminal end and is fused to sumo. Using the same protocol as described above, this fusion protein is expressed, purified and cleaved by Sumo protease to produce the N-terminal 16 residue deleted angtensinogen. Referring to FIG. 7, ligation of the N-terminal 16 residue deleted angtensinogen to the FITC-DRVYIHPFHLVIHNEST-thioester, a slightly different version of FITC-angiotensinogen is produced. FIG. 7 illustrates the sequence and FITC labeling of the N-terminal deleted Angiotensinogen, whereby (A) shows an amino acid sequence of N-terminal deleted angiotensinogen, and (B) shows the N-terminal FITC labeling of N-terminal deleted angiotensinogen of the invention. Cleavage of this FITC-angiotensinogen by Renin may be measured by recording fluorescence polarization signal as a function of time, as shown in FIG. 8. Trace B in FIG. 8 shows that when RRPFH-Sta-IHK, a renin specific inhibitor, is included in the cleavage reaction at the final concentration of 10 uM, fluorescence polarization showed little change. This proves that the FITC-angiotensinogen may be used as a substrate for Renin activity assay by recording the fluorescence polarization and the assay may be used to identify its inhibitors.

EXAMPLE 3

Figure 9:
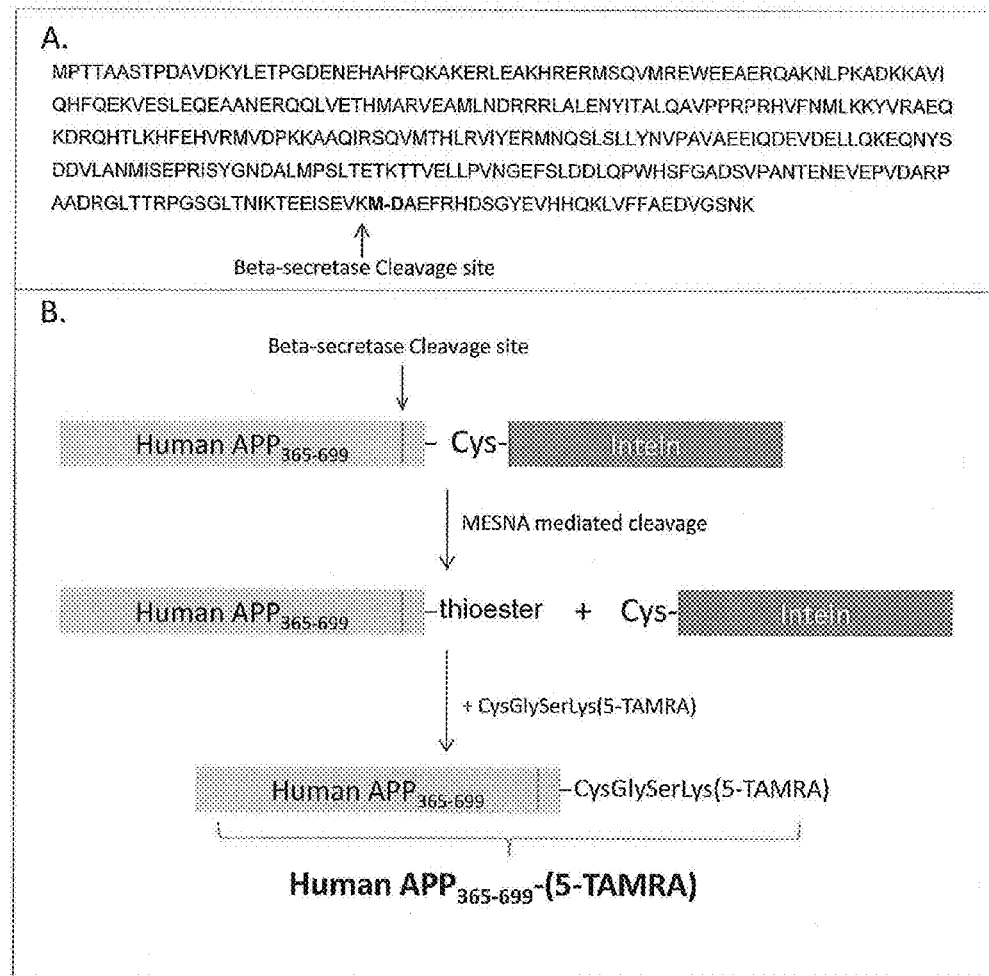
FIG. 9 illustrates the sequence and 5-TAMRA labeling of $APP_{365-699}$, whereby (A) shows an amino acid sequence of $APP_{365-699}$, and (B) shows the C-terminal 5-TAMRA labeling of $APP_{365-699}$ of the invention.
Figure 10:
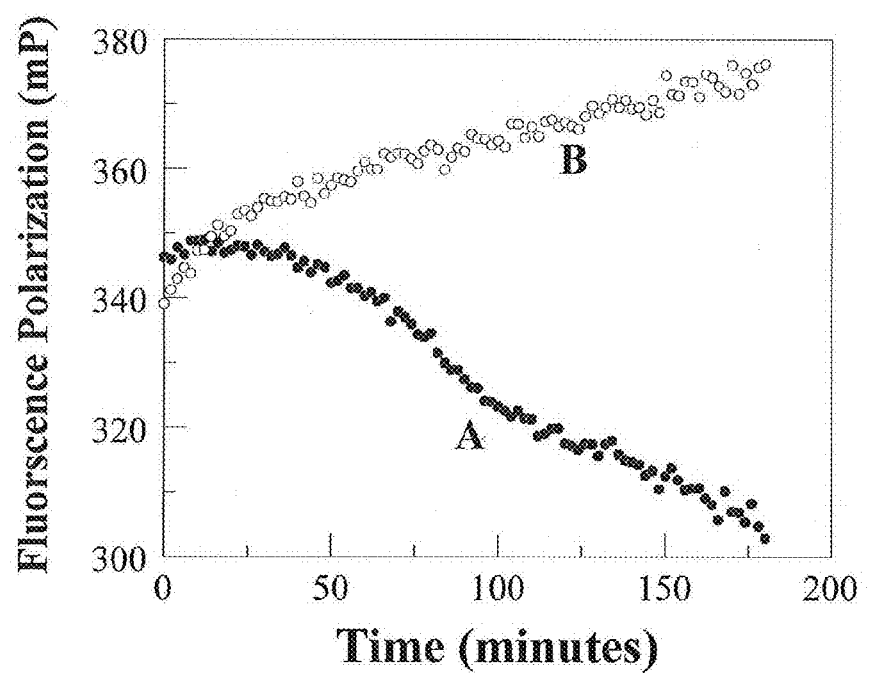
FIG. 10 illustrates the time course of Fluorescence Polarization of $APP_{365-699}$-(5-TAMRA) by BACE, whereby (A) shows the – inhibitor and (B) shows the + inhibitor of the invention.
Figure 11:
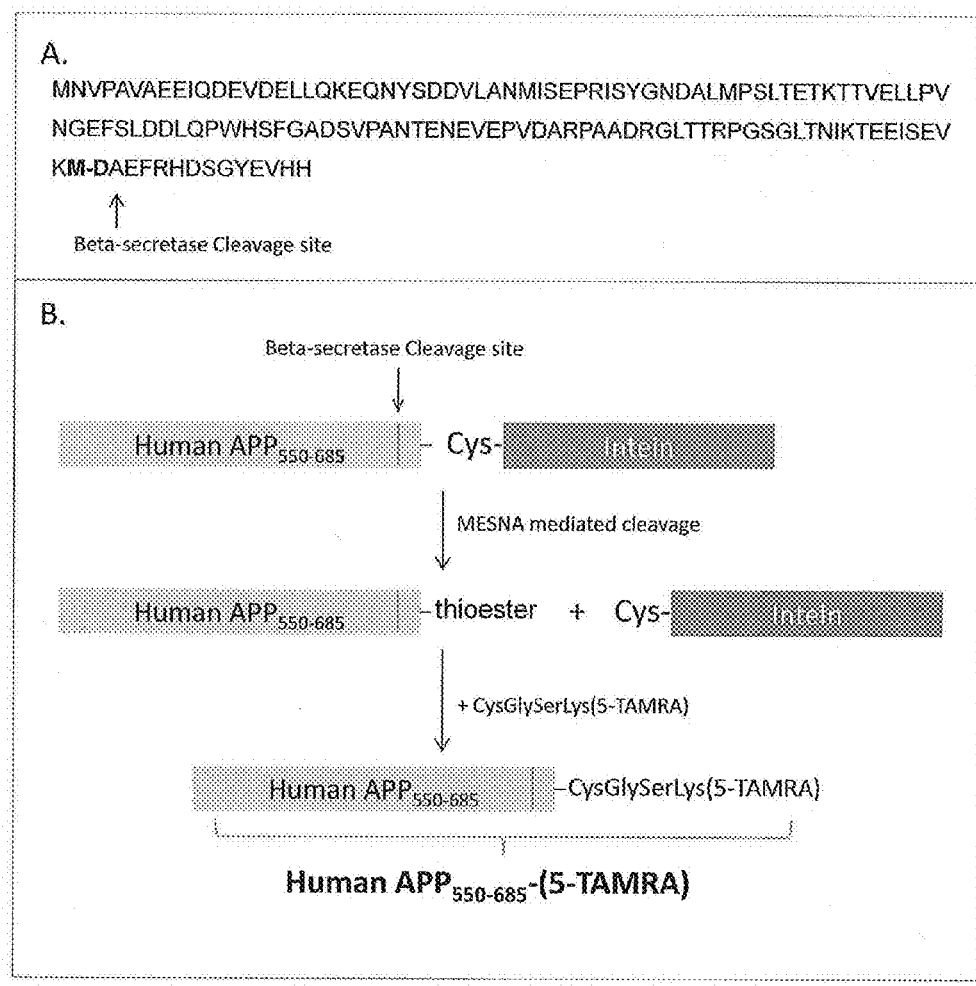
FIG. 11 illustrates the sequence and 5-TAMRA labeling of $APP_{550-685}$, whereby (A) shows an amino acid sequence of $APP_{550-685}$, and (B) shows the C-terminal 5-TAMRA labeling of $APP_{550-685}$ of the invention

Referring to FIGS. 9-11, in this example Beta-secretase (BACE) is one of the two proteases that cleave amyloid precursor protein (APP) to produce amyloid peptide 1-42. Human APP is a 733 residue protein. Full length of APP is consisted of several domains. BACE cleaves APP between residue 671 and 672. In this example, a fluorescence dye is specifically conjugated to the C-terminal end of $APP_{365-699}$ that contains two independent folded domains. Gene encoding $APP_{365-699}$ is fused to the N-terminal end of intein. After MESNA mediated self cleavage between $APP_{365-699}$ and intein, a thioester group, is added to the C-terminal end of $APP_{365-699}$. A fluorescence dye conjugated small peptide, CysGlySerLys-[5-TAMRA], is then ligated to the C-terminal end of $APP_{365-699}$ to produce fluorescent dye labeled $APP_{365-699}$:

FIG. 9 illustrates the sequence and 5-TAMRA labeling of $APP_{365-699}$, whereby (A) shows an amino acid sequence of $APP_{365-699}$, and (B) shows the C-terminal 5-TAMRA labeling of $APP_{365-699}$ of the invention. As shown in FIG. 9, cleavage of $APP_{365-699}$-[5-TAMRA] by BACE releases the C-terminal part of $APP_{365-699}$-[5-TAMRA], DAEFRHDS-GYEVHHQKLVFFAEDVGSNKCGSL-[5-TAMRA], which has a smaller molecular weight than that of $APP_{365-699}$-[5-TAMRA]. As a result, fluorescence polarization of 5-TAMRA reduces. Trace A in FIG. 10 shows the time course of fluorescence polarization when $APP_{365-699}$-[5-TAMRA] is cleaved by BACE. It proves that $APP_{365-699}$-[5-TAMRA] may be used as a substrate for BACE activity assay by recording the fluorescence polarization. When KTEEISEVN-Sta-VAEF (Sta=statine), a BACE specific inhibitor, is included in the cleavage reaction, the fluorescence polarization remains unchanged, as shown by Trace B in FIG. 10. Thus, $APP_{365-699}$-[5-TAMRA] may be used as a substrate for BACE activity assay by recording the fluorescence polarization and the assay may be used to identify its inhibitors.

EXAMPLE 4

Figure 12:
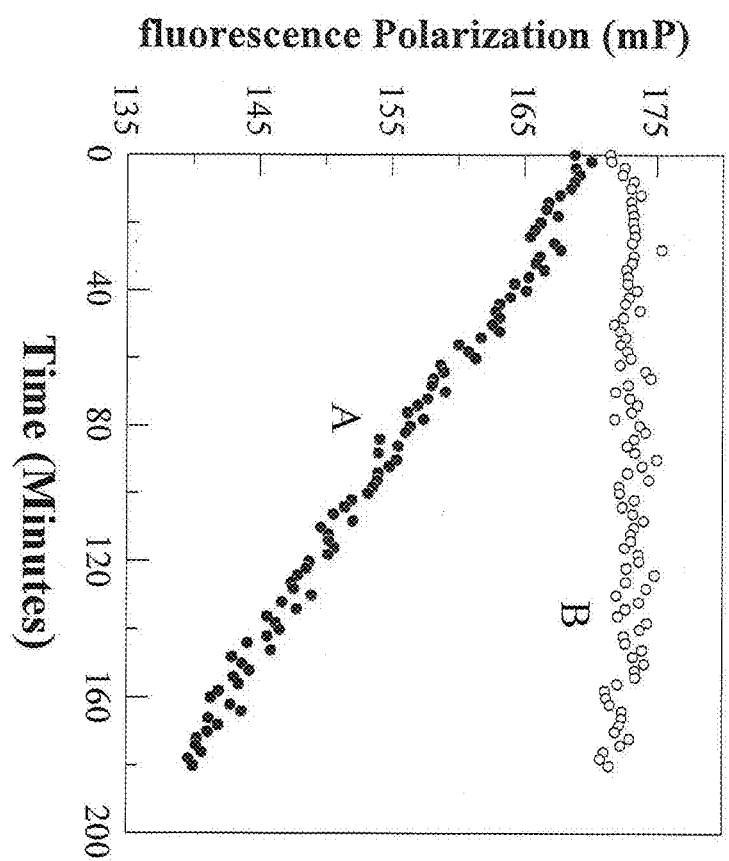
FIG. 12 illustrates the time course of Fluorescence Polarization of $APP_{550-685}$-(5-TAMRA) by BACE, whereby (A) shows the – inhibitor and (B) shows the + BACE specific inhibitor of the invention.

FIG. 11 illustrates the sequence and 5-TAMRA labeling of $APP_{550-685}$, whereby (A) shows an amino acid sequence of $APP_{550-685}$, and (B) shows the C-terminal 5-TAMRA labeling of $APP_{550-685}$ of the invention. In this example, a short version of APP that contains one domain of APP, $APP_{550-685}$, is labeled with a 5-TAMRA at its C-terminus using the same method as that of producing $APP_{365-699}$-[5-TAMRA]. FIG. 12 illustrates the time course of Fluorescence Polarization of $APP_{550-685}$-(5-TAMRA) by BACE, whereby (A) shows the – inhibitor and (B) shows the + BACE specific inhibitor of the invention. The results of FIG. 12 exhibit that $APP_{550-685}$-[5-TAMRA] may serve as a substrate for BACE activity assay by recording the fluorescence polarization and the assay may be used to identify its inhibitors.

EXAMPLE 5

This example uses FITC-(pro-TNF-α) to demonstrate that compounds interacting with the full length protein substrate may be discovered by the present assay methods. Compound 6,7-Dimethyl-3-((methyl-(2-(methyl-(1-(3-trifluoromethyl-phenyl)-1H-indol-3-ylmethyl)-amino)-ethyl)-amino)-methyl)-chromen-4-one is known as TNF-α inhibitor. This compound binds to TNF-α and inhibits the binding of TNF-α to its receptor. In this example, it is shown that such compound may also inhibit the cleavage of pro-TNF-α by ADAM 17. When 200 uM of this compound is pre-incubated with FITC-(pro-TNF-α) for 30 minutes, the cleavage rate of FITC-(pro-TNF-α) by ADAM 17 is reduced.

Referring to FIGS. 13 and 14, the fluorescence polarization assay results and SDS-PAGE results are shown, respectively. FIG. 13 illustrates the time course of Fluorescence Polarization of FITC-(pro-TNF alpha) Cleaved by ADAM 17, whereby (A) shows the – inhibitor and (B) shows the + TNF-alpha inhibitor of the invention. In FIG. 14, the SDS-PAGE results of FITC-(pro-TNF alpha) cleaved by ADAM 17 are shown, whereby (A) shows the fluorescence of FITC labeled pro-TNF-alpha and (B) shows the Coomassie brilliant blue staining. In FIG. 14, the lanes shown include: Lane 1, FITC-(pro-TNF-alpha); Lane 2, Cleavage reaction of FITC-(pro-TNF-alpha) by ADAM 17,180 minutes; Lane 3, FITC-(pro-TNF-alpha)+200 uM TNF-alpha inhibitor; and Lane 4, Cleavage reaction of FITC-(pro-TNF-alpha)+200 uM TNF-alpha inhibitor by ADAM 17,180 minutes of the invention.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for a protein based assay:
providing a full length protein substrate;
attaching a detection component to an N-terminal of the full length protein substrate to provide a site-specifically labeled full length protein substrate;
interacting the site-specifically labeled full length protein substrate with an analyte of interest that is assigned to a protease; and
providing a compound targeted for binding at least to the protease;
performing an assay using the site-specifically labeled full length protein substrate and the analyte of interest to determine whether said compound binds at least to the protease.

2. The method of claim 1 wherein the detection component comprises a fluorescent that provides a site-specifically labeled fluorescent protein substrate.

3. The method of claim 2 wherein the site-specifically labeled fluorescent protein substrate is generated by protein ligation by ligating the full length protein substrate with a fluorescence labeled peptide.

4. The method of claim 2 wherein the assay is performed by monitoring change of fluorescence signal continuously or after the end of reaction by methods selected from fluorescence intensity and fluorescence polarization.

5. The method of claim 1 wherein the assay for drug discovery discovers a compound that interacts with the analyte of interest or a compound that interacts with the site-specifically labeled full length protein substrate.

6. The method of claim 1 wherein the full length protein substrate comprises a protein that provides a site-specifically labeled protease substrate.

7. The method of claim 6 wherein the assay for drug discovery discovers a compound that interacts with the site-specifically labeled protease substrate.

8. The method of claim 1 wherein the detection component comprises a fluorescence dye or a quencher.

9. The method of claim 1 further including cleaving the full length protein substrate and attaching the detection component to a specific site of the full length protein substrate.

10. The method of claim 8 wherein a first end of the cleaved site is labeled with a fluorescent.

11. The method of claim 9 wherein a second end of the cleaved site, opposite to that of the first end of the cleaved site, is labeled with a quencher of the fluorescent.

12. A method for a protein based assay:
providing an independent folded domain of a protein substrate;
attaching a detection component to a C-terminal of the independent folded domain protein substrate to provide a site-specifically labeled independent folded domain protein substrate;
interacting the site-specifically labeled independent folded domain protein substrate with an analyte of interest that is assigned to a protease;
providing a compound targeted for binding at least to the protease;
performing an assay using the site-specifically labeled independent folded domain protein substrate and the analyte of interest to determine whether said compound binds at least to the protease.

13. The method of claim 12 further including cleaving the independent folded domain of the protein substrate and attaching the detection component to a specific site thereof.

14. The method of claim 13 wherein a first end of the cleaved site is labeled with a fluorescent.

15. The method of claim 14 wherein a second end of the cleaved site, opposite to that of the first end of the cleaved site, is labeled with a quencher of the fluorescent.

16. The method of claim 12 wherein the detection component comprises a fluorescent that provides a site-specifically labeled fluorescent independent folded domain of the protein substrate.

17. The method of claim 12 wherein the assay for drug discovery discovers a compound that interacts with the protease.

18. The method of claim 12 wherein the assay is performed by monitoring change of fluorescence signal continuously or after the end of reaction.

19. The method of claim 12 wherein the detection component comprises a fluorescence dye and its quencher.

20. The method of claim 12 wherein the assay for drug discovery discovers a compound that interacts with the analyte of interest or a compound that interacts with the site-specifically labeled independent folded domain of the protein substrate.

* * * * *